United States Patent
Aoun

(10) Patent No.: US 8,173,197 B2
(45) Date of Patent: May 8, 2012

(54) COATED MEDICAL DEVICES AND METHODS OF MAKING SAME

(75) Inventor: Walid Abi Aoun, Wantage (GB)

(73) Assignee: Puricore, Inc., Malvern, PA (US)

(*) Notice: Subject to any disclaimer, the term of this patent is extended or adjusted under 35 U.S.C. 154(b) by 1308 days.

(21) Appl. No.: 11/835,813

(22) Filed: Aug. 8, 2007

(65) Prior Publication Data

US 2008/0075832 A1    Mar. 27, 2008

Related U.S. Application Data

(60) Provisional application No. 60/836,380, filed on Aug. 9, 2006.

(51) Int. Cl.
| | |
|---|---|
| *B05D 5/00* | (2006.01) |
| *B05D 7/26* | (2006.01) |
| *B05D 1/36* | (2006.01) |
| *A61L 29/12* | (2006.01) |
| *A61L 31/12* | (2006.01) |
| *A61L 2/00* | (2006.01) |

(52) U.S. Cl. ..................... 427/2.1; 427/407.1

(58) Field of Classification Search .................. 427/2.1, 427/2.28, 2.3, 407.1, 407.2, 409, 412.1–412.5
See application file for complete search history.

(56) References Cited

U.S. PATENT DOCUMENTS

| 4,001,065 A | * | 1/1977 | Penneck et al. ................. 156/86 |
| 5,110,645 A | * | 5/1992 | Matsumoto et al. ......... 428/36.9 |
| 5,685,825 A | * | 11/1997 | Takase et al. ................. 600/140 |
| 5,876,331 A | * | 3/1999 | Wu et al. ....................... 600/139 |
| 2002/0051730 A1 | * | 5/2002 | Bodnar et al. .................. 422/33 |
| 2005/0159558 A1 | * | 7/2005 | Govaerts et al. ........... 525/326.3 |
| 2005/0260331 A1 | * | 11/2005 | Wang et al. .................... 427/2.1 |
| 2005/0267262 A1 | * | 12/2005 | Wagman et al. ............... 525/242 |
| 2006/0136051 A1 | * | 6/2006 | Furst et al. ................... 623/1.42 |
| 2008/0220274 A1 | * | 9/2008 | Cohen et al. .................. 428/500 |

FOREIGN PATENT DOCUMENTS

| GB | 2 316 090 | 2/1998 |
| JP | 11-137510 | 5/1999 |

OTHER PUBLICATIONS

International Preliminary Report on Patentability for PCT/US2007/075568 issued Feb. 10, 2009, 6 pages.*

* cited by examiner

*Primary Examiner* — William Phillip Fletcher, III
(74) *Attorney, Agent, or Firm* — Stradley Ronon Stevens & Young, LLP

(57) ABSTRACT

Methods of protecting an insertable medical device from chemical degradation are provided. Methods include coating the insertable medical device with an acrylic layer and then coating the acrylic layer with an acrylic-grafted fluoropolymer. Medical devices coated with oxidation-resistant coatings are also provided.

20 Claims, 1 Drawing Sheet

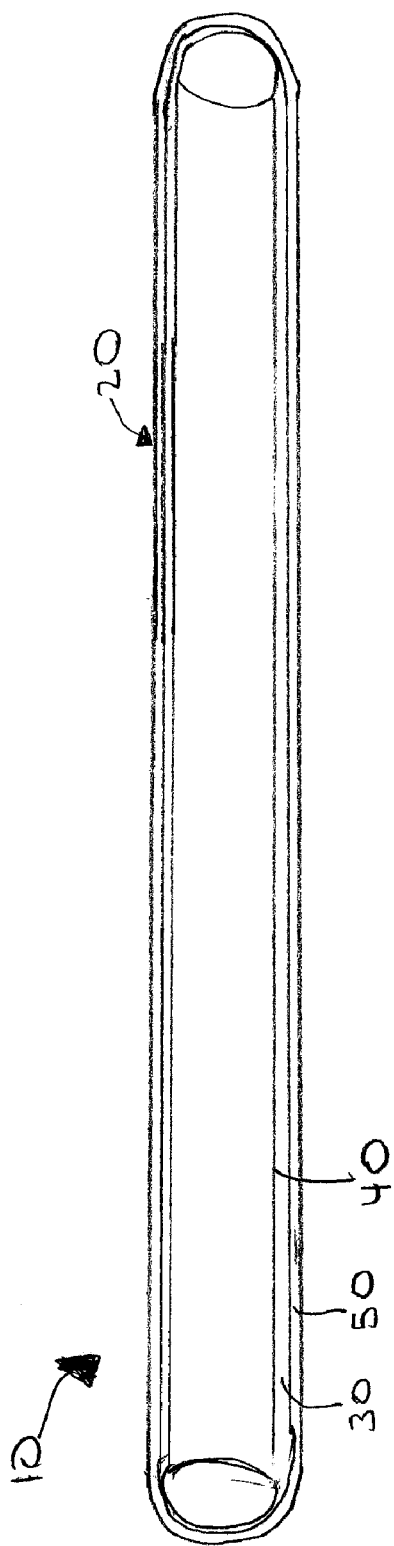

COATED MEDICAL DEVICES AND METHODS OF MAKING SAME

CROSS-REFERENCE TO RELATED APPLICATIONS

The present application claims priority to U.S. Provisional Application No. 60/836,380 filed on Aug. 9, 2006, which is incorporated by reference herein.

FIELD OF THE INVENTION

The present application is directed to coated medical devices that are protected from degradation by a disinfecting or sterilizing solution and methods of coating an insertable medical device to accomplish the same.

BACKGROUND OF THE INVENTION

Reuseable medical devices generally require disinfection or sterilization between uses. One way to sterilize a reuseable medical device is to expose the device to steam at high temperatures and pressures, i.e. autoclaving. This method, however, is often unsuitable for delicate medical apparatus, such as endoscopes, which may include components that are not heat-resistant. As an alternative, organic sterilizing/disinfecting solutions, such as glutaraldehyde, have been used at ambient temperatures. Glutaraldehyde, however, has limited sterilizing/disinfecting activity and may also cause allergic reactions in patients. Another alternative has been oxidizing sterilizing/disinfecting solutions, such as peracetic acid, hypochlorous acid, or chlorine dioxide. One way to prepare such oxidizing solutions has been through electrochemical processing of aqueous salt solutions as described, for example, in GB 2316090. These oxidizing solutions, such as STERILOX™, are produced by electrochemical cells comprising an anode chamber and a cathode chamber separated by a semi-permeable membrane and include oxidized chlorine species such as hypochlorous acid as sterilizing agents. Such solutions are highly effective in their sterilizing action, but are more aggressive than glultaraldehyde, for example, and may attack the plastic and similar components of medical devices.

The flexible sections of many reusable medical devices, such as endoscopes, are typically provided with polyurethane-based coatings to provide a protective coating and improve the handling properties of the medical device. However, many polyester- or polyether-based polyurethanes are not sufficiently resistant to degradation by oxidizing agents used as sterilants.

One approach to protect this protective coating is by providing an internal vapor barrier layer between the external polyurethane coating and the inner components, such as the optic fibers of an endoscope. (See U.S. Pat. No. 5,876,331). The endoscope may be sterilized by an oxidizing solution in the vapor phase, with the internal vapor barrier layer serving to keep the sterilizing vapor away from lubricants which may be provided in the inner components of the endoscope since a chemical reaction therebetween may otherwise form acids which could attack the polyurethane outer coating. Another approach to protecting the outer coating of a medical device is applying a urethane-silicone copolymer layer to the outer surface of the medical device. (See Japanese Application No. 9-305814 published as No. 11-137510). Such a coating comprises a mixture of a silicone resin and an aliphatic urethane polymer and an aromatic urethane polymer. However, the resistance of this material to hypochlorous acid-based disinfectants has not been found to be adequate.

Therefore, a need exists for protecting the outer coating of an insertable medical device from degradation by a sterilizing solution while maintaining the handling properties of the medical device.

SUMMARY OF THE INVENTION

The present invention provides coatings, coated medical devices, and methods of coating insertable medical devices.

In certain embodiments, the present invention provides a coating for an insertable medical device comprising an acrylic layer and an acrylic-grafted fluoropolymeric layer disposed on the acrylic layer. The coating substantially protects the insertable medical device from degradation by a sterilizing solution and substantially maintains the flexibility of the insertable medical device. The present invention also provides medical devices having such coating disposed thereon (which includes disposed on only a portion of the body of the medical device).

In certain embodiments, the present invention provides a method of coating an insertable medical device comprising providing an insertable medical device comprising a body and applying an acrylic layer to the body. The method further comprises applying to the acrylic layer an acrylic-grafted fluoropolymeric layer. The flexibility of the insertable medical device is substantially unaltered and the medical device is substantially protected from degradation by a sterilizing solution.

In certain embodiments, the present invention provides a method of coating an insertable medical device comprising providing an insertable medical device comprising a body and applying an acrylic layer to the body. The method further applying to the acrylic layer a fluoropolymeric layer comprising a fluoropolymer having acrylic groups grafted thereon, the fluoropolymer having a melt flow index in the range of about 1 gram/10 minutes to about 5 grams/10 minutes measured at 230° C. with a 10 kilogram weight, the acrylic groups present in an amount between about 3 to 11 wt % of the total weight of the fluoropolymer.

In certain embodiments, the present invention provides a method of coating an insertable medical device comprising providing an insertable medical device comprising a body and applying an acrylic layer to the body. The method further comprises applying to the acrylic layer a fluoropolymeric layer comprising a fluoropolymer having acrylic groups grafted thereon, the fluoropolymer having a melt flow index in the range of about 20 grams/10 minutes to about 30 grams/10 minutes measured at 230° C. with a 5 kilogram weight, the acrylic groups present in an amount between about 3 to 11 wt % of the total weight of the fluoropolymer.

In certain embodiments, the present invention provides a method of coating an insertable medical device comprising providing an insertable medical device comprising a body and applying an acrylic layer to the body. The method further comprises applying to the acrylic layer a fluoropolymeric layer comprising a fluoropolymer having acrylic groups grafted thereon, the fluoropolymer having a melt flow index in the range of about 2 grams/10 minutes to about 10 grams/10 minutes measured at 230° C. with a 2.16 kilogram weight, the acrylic groups present in an amount between about 3 to 11 wt % of the total weight of the fluoropolymer.

In certain embodiments, the present invention provides a method of coating an insertable medical device comprising providing an insertable medical device comprising a body, grafting acrylic groups with a graft weight between 3% and 11% onto the body and applying a layer onto the body comprising a fluoroelastomer with a melt flow index, measured at 230° C., of about 1.3 grams/10 minutes with a 10 kilogram weight, about 24 grams/10 minute with a 5 kilogram weight, or about 8 grams/10 minute with a 2.16 kilogram weight.

BRIEF DESCRIPTION OF THE DRAWING

FIG. 1 is a schematic illustration of a medical device comprising a coating according to an embodiment of the present invention.

DETAILED DESCRIPTION OF THE INVENTION

The present invention provides methods of coating an insertable medical device to substantially protect the medical device from degradation by an oxidizing solution. Preferably, the methods also allow the medical device to substantially maintain its original flexibility as measured prior to the coating process. In certain embodiments, the present invention provides a method of coating an insertable medical device by applying an acrylic layer to the body of the medical device and then applying an acrylic-grafted fluoropolymeric layer on the acrylic layer. FIG. 1 is a schematic illustration of a medical device 10 having a coating 20 prepared according to the above-described method. Specifically, coating 20 comprising an acrylic base layer 30 over the outer surface of body 40 of medical device 10. Coating 20 further comprises an acrylic-grafted fluoropolymeric layer 50 over the acrylic base layer 30.

Regarding applying an acrylic layer to the body of a medical device, a mixture comprising an acrylic compound may be prepared or otherwise obtained and then applied to the body of a medical device. Non-limiting examples of suitable acrylic compounds include acrylic polyurethane, styrene butadiene rubber with acrylic acid, acrylic silicones, and acrylic polyesters. The acrylic compound can be in a dispersion, suspension or a solution. For example, the acrylic compound can be dissolved in a solvent and applied as a solution to the body of the medical device. Suitable solvents to serve this function include, for example, water, isopropyl alcohol, toluene, acetone, or methyl-ethyl ketone. The mixture comprising an acrylic compound can be applied to the body of the medical device by any suitable method known in the art, such as, for example, dipping, spraying, rolling, brushing, or vapor deposition. After applying the acrylic mixture, the body of the medical device can be dried to form an acrylic layer.

After applying an acrylic layer to the body of a medical device, certain embodiments of methods of the present invention provide for applying an acrylic-grafted fluoropolymer layer on the acrylic layer. Non-limiting examples of fluoropolymers that are suitable for use include fluorinated polymers or copolymers having elastomeric properties (fluoroelastomers). For example, fluoroelastomers that may be suitable for use in the present invention include those produced from the monomers vinylidene fluoride ($CH_2=CF_2$), hexafluoropropylene ($CF_2=CFCF_3$), and chlorotrifluoroethylene ($CF_2=CFCl$), or tetrafluoroethylene. Other non-limiting examples of fluoroelastomers include the polyvinylidene fluoride (PVDF) family of polymers, the polyvinyl fluoride family of polymers, and the fluorourethane family of polymers Other polymers that could be used include fluoroethylene propylene, fluoro-perfluoro ether copolymers and terpolymers. In certain embodiments, in order to have the desired flexibility, the selected polymer has a melt flow index (ASTM D 1238) of 1 gram/10 minutes to about 5 gram/0 minutes measured at 230° C. with a 10 kg weight, 20 grams/ 10 minutes to about 30 grams/10 minutes measured at 230° C. with a 5 kg weight, or 2 grams/10 minutes to about 10 grams/ 10 minutes measured at 230° C. with a 2.16 kg weight. Preferably, the melt flow index is about 1.3 grams/10 minute measured at 230° C. with a 10 kg weight, about 24 grams/10 minutes at 230° C. with a 5 kg weight, or about 8 grams/10 minutes at 230° C. with a 2.16 kg weight.

The chemical inertness of a fluoropolymer can hamper its adhesion to the acrylic layer of the medical device. Further, the fluoropolymer may be unable to produce a glossy finish and may have insufficient scratching and marring resistance. As such, in certain embodiments, a functional group can be added to the fluoropolymer to optimize its performance. For example, in certain embodiments, an acrylic group is grafted onto the fluoropolymer backbone. These acrylic groups not only have good compatibility with fluoropolymers, but are also polar in nature and tend to stick well to polar substrates, such as an acrylic layer, to provide better adhesion. Further, these acrylic groups grafted onto the fluoropolymer are crosslinkable and can deliver good resistance to varying temperature ranges, chemicals, ultraviolet light and oxidation. Non-limiting examples of acrylic compounds with acrylic groups that can be grafted on a fluoropolymer to interact with the acrylic groups of the acrylic layer include dimethyl acrylamide, butyl acrylate, methyl acrylate, ethyl acrylate, isopropyl acrylate, and isobutyl acrylate. The acrylic groups can also include, for example, acrylic substituted alcohol groups, methacrylic groups, and acrylamides.

The weight of the acrylic compound graft should be such that the grafted fluoropolymer adheres to the acrylic layer of the medical device but also protects the medical device from sterilizing agents that could penetrate through the acrylic sites to the surface of the medical device and cause degradation of the medical device. In certain embodiments, the weight of the acrylic compound graft is between 3% to 11% based on the final grafted fluoropolymer weight in order to achieve good adhesion properties. Preferably, the weight of the acrylic compound graft is between 5% to 6% based on the final grafted fluoropolymer weight.

The acrylic-grafted fluoropolymer can be in a dispersion, suspension or a solution. For example, the acrylic compound and the fluoropolymer can be dissolved in a single solvent or separate solvents and applied as a solution to the acrylic layer disposed on the body of the medical device. Suitable solvents to serve this function include, for example, methyl-ethyl ketone, dimethyl formamide, 1-methyl-2-pyrrolidone, di-methylacetamide, or tetrahydrofuran. The acrylic-grafted fluoropolymer mixture can be applied to the body of the medical device by any suitable method known in the art, such as, for example, dipping, spraying, rolling, brushing, or vapor deposition. After applying the mixture, the body of the medical device can be dried to form an acrylic-grafted fluoropolymer layer.

The medical devices on which the above-described layers are applied can be any insertable medical device known in the art that is suitable for insertion in a human or animal body, is reusable, and may require sterilization. Non-limiting examples of such medical devices include catheters and endoscopes. In certain embodiments, the medical device is fabricated from polyurethane or at least has a polyurethane outer coating.

In certain embodiments, the medical device is coated such that its flexibility is substantially unaltered and it is substantially protected from degradation by a sterilizing solution. By "substantially unaltered" is meant that the medical device's resistance to bending after coating is within the same order of magnitude as the medical device's resistance to bending prior to coating. The medical device's resistance to bending can be determined by any suitable mechanism known in the art such as by using a three-point bend test where the medical device is held in place with two probes and a third probe applies pressure at the mid-point between the other two probes. The peak force of the medical device can thus be measured and provides an indication of flexibility. In preferred embodiments, the coating is able to withstand stress cracking for at least 50 uses. By "substantially protected from degradation" is meant that if the coating were exposed during a disinfection or sterilizing cycle to an oxidizing solution having a free available chlorine concentration of approximately 220 ppm, the coating would withstand the chemical degradation effect of such oxidizing solution on the surface of the medical device beneath the coating for at least 500 disinfection or sterilizing cycles of the medical device. In other words, the medical device is "substantially protected from degradation" if a sterilizing solution having a free available chlorine concentration of approximately 220 ppm does not significantly damage the coating after the medical device has been exposed to the sterilizing solution at least 500 times such that the medical device maintains its functionality. Typically, but not exclusively, the surface of the medical device is fabricated from polyurethane. Of course, the medical device could also be substantially protected from degradation by other sterilizing solutions, such as solutions having a free available concentration between 100-1,000 ppm and specifically 450 ppm, 500 ppm, 600 ppm and/or 650 ppm.

Solutions that the coating may protect against include sterilizing solutions (including oxidizing sterilants) such as hydrogen peroxide, ozone, chlorine dioxide, peracetic acid, and hypochlorous acid. In certain embodiments, the sterilizing solution is hypochlorous acid having an free available chlorine concentration of 220 ppm. In certain other embodiments, the sterilizing solution is hypochlorous acid having a free available concentration of about 650 ppm.

EXAMPLES

Example 1

The following example indicates how the flexibility of a polyurethane tube is substantially unaltered after coating the tube with an acrylic layer and then a fluoropolymeric layer.

Polyurethane tubes, each 120 centimeters (cm) long, are sprayed at least once with an aqueous acrylic coating (a polyurethane-acrylic hybrid dispersion) followed by a fluorinated top coating ($VF_2$-HFP). Two polyurethane tube remains uncoated and serves a controls. All tubes, including the controls are cured at 50° C., to allow solvent evaporation and straightening.

The flexibility of each coated and uncoated polyurethane tube is assessed by applying a series of flexion forces across the tube at 20 cm intervals along its length using a Lutron FG-5000 force gauge. Each tube, in turn, is passively supported in a three point jig and the measuring flexion point is allowed to passively contact the tube. At this point, the force gauge is set to read zero grams. The force gauge is also set to read the peak force and then 10 rotations of the jig are made over 10 seconds thus flexing the tube. The peak force over 10 rotations (in grams) is recorded. The measurements are recorded under a constant temperature of 23° C.-26° C. and a relative humidity of less than 60%. The force gauge measurements for the various coated polyurethane tubes are provided in Table 1. The results indicate that the peak force of the polyurethane tube coated with an acrylic primer and then coated with a fluoropolymer is within the same order of magnitude as the peak force of the uncoated polyurethane tubes.

TABLE 1

| Tube Code or Coating | Average Peak force (g) of 6 readings | Standard Deviation |
| --- | --- | --- |
| 107/8 Blank | 380 | 9.8 |
| 107/13 Blank | 391 | 6.7 |
| 107/13L Incorez W2600/with 3 coats of Solef PVDF 21216 | 510 | 5.3 |

Example 2

The following example describes how an insertion tube and light guide tube are substantially protected from degradation by an oxidizing solution after coating with an acrylic layer and then a fluoropolymeric layer.

An insertion tube and a light guide tube are coated with a polyurethane acrylic primer in an aqueous suspension and then coated with a PVDF copolymer ($VF_2$-HFP). Both tubes are repeatedly subjected to the following cleansing cycle: manually wash in warm water and detergent; automatic wash with detergent for 3 minutes; rinse for 90 seconds; disinfection with an oxidizing solution having an AFC concentration of 250 ppm (STERILOX™, PuriCore Technologies) for five minutes; and final rinse for 90 seconds. The insertion tube suffers no damage to the outer lacquer finish after 290 cycles and the light guide tube suffers no damage to the outer lacquer finish after 138 cycles.

Example 3

The following example describes how an insertion tube is substantially protected from degradation by an oxidizing solution after coating with an acrylic layer and then a fluoropolymeric layer having an acrylic group grafted thereon.

An insertion tube was coated with a primer made from a styrene butadiene rubber (SBR) with added acrylic groups (5-6%). The SBR was sprayed on the tube and allowed to cure at 50° C. for about 1 hour. A top coat of PVDF with acrylic acid (5-6% by weight) was sprayed and the tube was kept at 60° C. for 6 to 8 hours to allow the solvent to evaporate completely. The tube was subjected to a series of complete immersion in an electrolyzed saline solution (STERILOX™, PuriCore, Inc., Malvern, Pa.) at a concentration of 250 ppm for at least 1 hour at a time (equivalent to 20 sterilization cycles). After an equivalent of 400 cycles, the insertion tube did not suffer any damage to the outer lacquer.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons killed in the art and such modifications are within the scope of the present invention. Furthermore, all references cited herein are incorporated by reference in their entirety.

I claim:

1. A method of coating a reusable insertable medical device comprising:
   providing a reusable insertable medical device comprising a body;
   applying an acrylic layer to the body; and
   applying onto the acrylic layer an acrylic-grafted fluoropolymeric layer comprising a fluoropolymer having acrylic groups grafted thereon, wherein the flexibility of the reusable insertable medical device is substantially unaltered; and
   substantially protecting the reusable insertable medical device from degradation upon exposure to an oxidizing solution.

2. The method of claim 1, wherein the fluoropolymer comprises a fluoroelastomer.

3. The method according to claim 2, wherein the fluoroelastomer is a poly(vinylidene fluoride) polymer.

4. The method according to claim 2, wherein the fluoroelastomer comprises hexafluoropropylene, tetrafluoroethylene, perfluoromethylvinylether, or chlorotrifluoroethylene.

5. The method according to claim 2, wherein the fluoroelastomer is a copolymer comprising vinylidene fluoride and at least one other fluorinated monomer.

6. The method according to claim 2, wherein the fluoroelastomer comprises at least one of a hexafluoropropylene, tetrafluoroethylene, perfluoromethylvinylether, and chlorotrifluoroethylene.

7. The method of claim 2 wherein the substantially protecting comprises withstanding chemical degradation upon exposure during disinfection or sterilizing to the oxidizing solution on a surface of the medical device beneath the layers for at least 500 disinfection or sterilizing cycles of the medical device.

8. The method according to claim 1, wherein the fluoropolymer has a melt flow index about 1.3 grams/10 minutes measured at 230° C. using a 10 kilogram weight.

9. The method according to claim 1, wherein the fluoropolymer has a melt flow index about 24 grams/10 minutes measured at 230° C. using a 5 kilogram weight.

10. The method according to claim 1, wherein the fluoropolymer has a melt flow index about 8 grams/10 minutes measured at 230° C. using a 2.16 kilogram weight.

11. The method according to claim 1, wherein the graft weight of the acrylic groups is between 3% and 11%.

12. The method according to claim 11, wherein the acrylic groups are acrylic acid, dimethyl acrylamide, butyl acrylate, or methyl acrylate.

13. The method of claim 1, wherein the insertable medical device is an endoscope.

14. A method of coating a reusable insertable medical device comprising:
   providing a reusable insertable medical device comprising a body;
   applying an acrylic layer to the body; and
   applying onto the acrylic layer an acrylic-grafted fluoropolymeric layer comprising a fluoropolymer having acrylic groups grafted thereon, the fluoropolymer having a melt flow index in the range of about 1 grams/10 minutes to about 5 grams/10 minutes measured at 230° C. with a 10 kilogram weight, the acrylic groups present in an amount between about 3 to 11 wt % of the total weight of the fluoropolymer.

15. The method of claim 14 further comprising:
   substantially protecting the insertable medical device from degradation upon exposure to an oxidizing solution.

16. A method of coating a reusable insertable medical device comprising:
   providing a reusable insertable medical device comprising a body;
   applying an acrylic layer to the body; and
   applying onto the acrylic layer an acrylic-grafted fluoropolymeric layer comprising a fluoropolymer having acrylic groups grafted thereon, the fluoropolymer having a melt flow index in the range of about 20 grams/10 minutes to about 30 grams/10 minutes measured at 230° C. with a 5 kilogram weight, the acrylic groups present in an amount between about 3 to 11 wt % of the total weight of the fluoropolymer.

17. The method of claim 16 further comprising:
   substantially protecting the insertable medical device from degradation upon exposure to an oxidizing solution.

18. A method of coating a reusable insertable medical device comprising:
   providing a reusable insertable medical device comprising a body;
   applying an acrylic layer to the body; and
   applying onto the acrylic layer an acrylic-grafted fluoropolymer layer comprising a fluoropolymer having acrylic groups grafted thereon, the fluoropolymer having a melt flow index in the range of about 2 grams/10 minutes to about 10 grams/10 minutes measured at 230° C. with a 2.16 kilogram weight, the acrylic groups present in an amount between about 3 to 11 wt % of the total weight of the fluoropolymer.

19. The method of claim 18 further comprising:
   substantially protecting the insertable medical device from degradation upon exposure to an oxidizing solution.

20. A method of coating a reusable insertable medical device comprising:
   providing a reusable insertable medical device comprising a body;
   applying an acrylic layer to the body;
   grafting acrylic groups with a graft weight between 3% and 11% onto a fluoroelastomer with a melt flow index, measured at 230° C., of about 1.3 grams/10 minutes with at 10 kilogram weight; about 24 grams/10 minutes with a 5 kilogram weight; or about 8 grams/10 minutes with a 2.16 kilogram weight; and
   applying the acrylic-grafted fluoroelastomer onto the body.

* * * * *